United States Patent [19]
Liddell et al.

[11] Patent Number: 6,146,879
[45] Date of Patent: *Nov. 14, 2000

[54] BIOCATALYSTS

[75] Inventors: John Macdonald Liddell, Eaglescliffe; William Greer, Billingham, both of United Kingdom

[73] Assignee: Zeneca Limited, London, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/968,091

[22] Filed: Nov. 12, 1997

Related U.S. Application Data

[60] Continuation of application No. 08/442,871, May 17, 1995, abandoned, which is a division of application No. 07/962,010, Oct. 15, 1992, abandoned, which is a continuation of application No. 07/424,998, Oct. 23, 1989, abandoned.

[30] Foreign Application Priority Data

Oct. 24, 1988 [GB] United Kingdom .................. 8824897

[51] Int. Cl.$^7$ ................................ C12N 1/04; C12N 9/98
[52] U.S. Cl. ........................................ 435/260; 435/187
[58] Field of Search ..................... 435/187, 260, 435/325

[56] References Cited

U.S. PATENT DOCUMENTS

| | | | |
|---|---|---|---|
| 3,615,685 | 10/1971 | Fantozzi et al. | 426/62 |
| 3,875,306 | 4/1975 | Alstrom | 426/61 |
| 3,897,307 | 7/1975 | Porubean et al. | 426/61 |
| 3,923,599 | 12/1975 | Hess et al. | 435/188 |
| 4,233,401 | 11/1980 | Neubeck | 435/187 |
| 4,521,254 | 6/1985 | Anderson et al. | 135/26 |
| 4,546,078 | 10/1985 | Manecke et al. | 435/52 |
| 4,617,272 | 10/1986 | Kirkwood et al. | 435/183 |
| 4,729,956 | 3/1988 | Hopkins | 435/188 |
| 4,755,468 | 7/1988 | Jung et al. | 435/178 |
| 4,758,518 | 7/1988 | Taylor | 435/195 |
| 4,886,664 | 12/1989 | Jung et al. | 424/93.4 |
| 4,894,341 | 1/1990 | Richardson | 435/227 |
| 4,925,797 | 5/1990 | Byrom et al. | 435/135 |
| 4,956,295 | 9/1990 | Sudoma | 426/61 |

FOREIGN PATENT DOCUMENTS

| | | |
|---|---|---|
| 366303 | 5/1990 | European Pat. Off. . |
| 2626626 | 12/1977 | Germany . |

OTHER PUBLICATIONS

Kalunyants et al, "Sensitivity of enzymes to high temperature during spray drying of their solutions", Chemical Abstracts, Aug. 2, 1971, vol. 75, No. 5, pp. 343.
Masters (1985) *Spray Drying Handbook, Fourth Edition*, by John Wiley & Sons (New York) Halsted Press, pp. 625–644.
Hjort et al., "Isolation and Characterization of a Nitrile Hydratase from a Rhizobium", J. Chem. Technol. Biotechnol., 48(2), pp. S.217–226, in Ceaba AN 70:9001935, 1990.

*Primary Examiner*—Jon P. Weber
*Attorney, Agent, or Firm*—Pillsbury Madison & Sutro LLP

[57] ABSTRACT

A method is presented for spray-drying whole microorganisms of *Fusarium lateritium*, *Methylophilus methylotrophus*, and *Pseudomonas putida* under conditions that the activity of cyanide hydratase, amidase and D-2-haloalkanoic acid halidohydrolase respectively are retained.

5 Claims, 1 Drawing Sheet

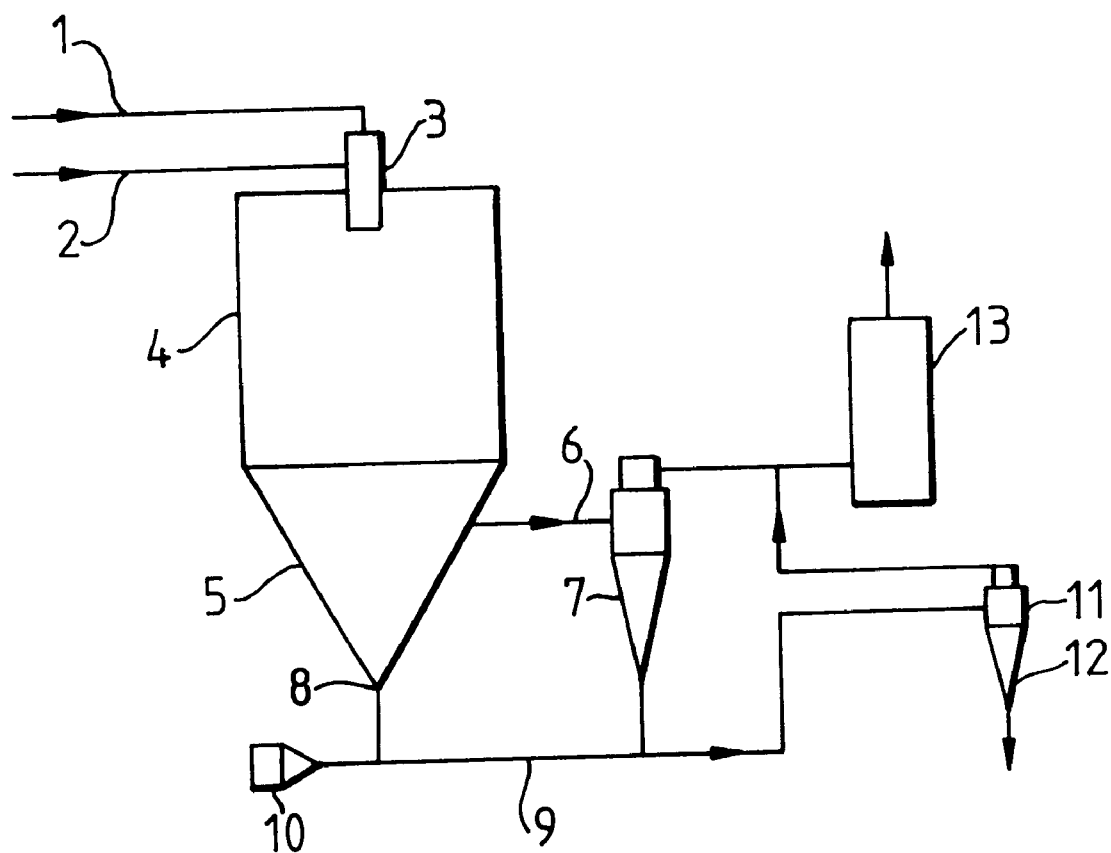

BIOCATALYSTS

This is a continuation of application Ser. No. 08/442,871, filed on May 17, 1995, which was abandoned upon the filing hereof which is a divisional of application Ser. No. 07/962,010, filed Oct. 15, 1992, now abandoned, which is a continuation of application Ser. No. 07/424,998, filed Oct. 23, 1989, now abandoned.

BACKGROUND OF THE INVENTION

This invention relates to biocatalysts, to a method for their production and to a biochemical process using such biocatalysts.

The microbiological sciences have developed rapidly during the past two decades and an increasing number of commercial biochemical processes have been developed using enzymes as biocatalysts. Examples of such biochemical processes include those described in our European Patent Specifications Nos. 76606 and 179603. In such processes the biocatalysts employed have an important role.

To date enzymes used as biocatalysts have generally been used in the forms; (a) purified enzymes; (b) wet suspensions of cells containing the enzymes; and (c) immobilised whole cells containing the enzymes. All three forms however have disadvantages which restrict their commercial applicability. Purified enzymes are very useful but are expensive to produce and their utility is restricted to processes producing high-value end products. Enzymes in wet cell suspensions lose their activity quickly. When such suspensions are to be stored even for short periods it is necessary to add other materials such as anti-freeze cryo-protectants to them and to cool to temperatures below 0° C. to prevent rupture of cells contained in the suspensions. With enzymes in immobilised whole cells it is difficult to maintain the full activity of the enzymes over long periods.

SUMMARY OF THE INVENTION

According to the present invention we provide enzyme-containing biocatalysts which have been produced by spray drying whole cells of enzyme-containing microorganisms under conditions such that the biocatalytic activity of the enzymes is retained.

Further according to the present invention we provide a method for the production of enzyme-containing biocatalysts which comprises a step wherein whole cells of enzyme-containing microorganisms are spray dried under conditions such that the biocatalytic activity of the enzymes is retained.

Further according to the present invention we provide a process for conducting a biochemical reaction in which an enzyme-containing biocatalyst is used wherein the enzyme containing biocatalyst has been produced by spray drying whole cells of an enzyme-containing microorganism under conditions such that the biocatalytic activity of the enzyme is retained.

BRIEF DESCRIPTION OF THE FIGURE

The FIGURE is a diagram of an apparatus for open cycle, co-current spray drying.

DETAILED DESCRIPTION OF THE INVENTION

A general feature of soluble proteins is that an irreversible denaturation occurs with loss of enzyme activity at higher temperatures. For any enzyme there is a temperature above which enzyme activity is rapidly lost. Thus for example many de-halogenase enzymes become inactive when the temperatures of solutions containing them rise above 50° C. It is therefore surprising that spray dried microorganisms can retain biocatalytic activity and spray drying techniques have not previously been used upon microorganism cells intended for use as biocatalysts. We believe that the retention of biocatalytic activity occurs because, although the temperatures used in spray drying are much higher than those at which inactivation normally occurs, the residence time of the cells at these high temperatures is short and in consequence the degree of inactivation is insignificant.

The method of the invention can be used to produce biocatalysts using yeasts or bacteria (particularly Gram-negative bacteria) and including strains produced by genetic modification. Biocatalysts can be produced containing any required enzyme. Enzymes which can very suitably be contained in the biocatalysts of the invention include cyanide hydratase, amidase, alcohol dehydrogenases and D-2-haloalkanoic acid halidohydrolase (D-2-HAA halidohydrolase). In particular the method of the invention may be used for the production of biocatalysts for use in the process of our European Patent Specification No. 179603 by spray drying cells of the following bacterial strains:
1. *Pseudomonas putida* NCIB 12018
2. *Pseudomonas fluorescens* NCIB 12159
3. NCIB 12160
4. NCIB 12161
5. *Pseudomonas putida* NCIB 12158.

Cultures of these strains have been deposited at The National Collections of Industrial and Marine Bacteria (NCIMB), PO Box 31, 135 Abbey Road, Aberdeen, UK.

Other commercially useful microorganism whose cells may be spray dried by the method of the invention include the following:

*Fusarium lateritium* Nees strain CMI 300533 described in EP 233719 and deposited, Feb. 3, 1986, at the Commonwealth Mycological Institute (CMI), Ferry Lane, Kew, Richmond, Surrey, England;

*Methylophilus methylotrophus* strain AS-1 (NCIB 10515) described in GB 1370892;

*Candida utilis* strain ATCC 8206 deposited at the American Type Culture Collection (ATCC), 12301 Parklawn Drive, Rockville, Md., 20852, USA; and

*Lactobacillus plantarum* strain NCIMB 40027

In spray drying a feed (usually aqueous) is atomized into a spray which is contacted with a drying medium (generally air) to cause moisture evaporation. Drying of the spray continues until the desired moisture content in the dried particles is obtained at which stage the product is recovered from the drying medium. The method of the invention can be carried out using any spray drying technique, e.g. using a pressure nozzle, a rotary atomiser or a two-fluid nozzle. Preferred spray drier inlet temperatures are in the range 140° C. to 250° C., particularly in the range 140° C. to 180° C. Preferred spray drier outlet temperatures are in the range 60° C. to 110° C., particularly in the range 60° C. to 90° C. It is preferred that spray drying is conducted in such a way that the period during which the cells are subjected to high temperatures is as brief as possible consistant with satisfactory drying being effected. Suitable average periods of exposure to higher temperatures are in the range 15 seconds to 45 seconds. The method of the invention is preferably applied to cell-containing suspensions with cell dry weights in the range 2% to 18%, particularly 6% to 12%.

The method of the invention can be carried out on a batch or continuous basis. The spray drying may be either a distinct process, carried out on cells produced in another process elsewhere, or a step in an overall process wherein the microorganism cells are supplied to the spray drier as they are produced in a fermenter and are thereafter harvested. The process of the invention may be applied in a wide variety of biochemical processes. In particular it can be applied in the process of our European Patent Specification No. 179603. The process of European Specification 179603 increases the concentration of the L-enantiomer of a 2-haloalkanoic acid in a mixture of the D- and L-enantiomers.

Spray dried cells produced by the method of the invention generally retain their enzyme activity for considerably longer periods than is the case with conventional wet cell suspensions. In particular spray dried cells can be stored for periods up to a year with negligible loss of activity. In contrast enzyme activity in wet cell suspensions declines steadily with time and becomes negligible after periods of only a few weeks, e.g. four to six weeks.

The method of the invention is illustrated in the accompanying FIGURE which is a diagram of an apparatus for open-cycle, co-current spray drying.

In the apparatus of the FIGURE a feed, comprising an aqueous suspension of microorganism cells containing the enzyme biocatalyst to be produced, and heated air are supplied along conduits 1 and 2 respectively to atomizer 3 in which the feed is atomised into a fine spray containing millions of individual droplets. Atomizer 3 is located in the upper end of drying chamber 4 and after the spray has been produced it passes into the drying chamber 4 and is dried. Following drying of the spray the majority of the dried product falls into the lower part 5 of drying chamber 4. The product fines remain entrained in the air and pass along exhaust drying air duct 6 to powder recovery cyclone 7 for separation. Thereafter the fines enter the pneumatic conveying system. From the lower part 5 of drying chamber 4 the majority of the product passes through powder take-off 8 into conduit 9 along which it is carried by conveying air, supplied from 10, to transport cyclone 11. The dried product (dried microorganism cells containing active enzyme biocatalyst) is finally removed from the apparatus at the lower end 12 of transport cyclone 11. Exhaust air from cyclones 7 and 11 passes to the atmosphere through scrubber 13.

The invention is illustrated by the following Examples:

EXAMPLE 1

The apparatus shown in the FIGURE was used to spray dry cells of the bacterium *Pseudomonas putida* NCIB 12018 containing the enzyme D-2-haloalkanoic acid halidohydrolase. The spray drier inlet temperature was 180° C. and the outlet temperature was 90° C. The retention of activity of the enzyme in hydrolysing D-chloropropionic acid to L-lactic acid over the spray drier was found to be 100%.

In storage it was found that the spray dried cells would retain 50% of the enzyme activity after six months on storage at room temperature. Enzyme activity was completely retained in storage for over 12 months at 4° C. and −20° C. This compares most favourably with the retention of activity by wet cells of the same microorganism. In the wet cells activity was lost within 3 weeks at 4° C.

EXAMPLE 2

The apparatus shown in the FIGURE was used to spray dry cells of the fungus *Fusarium lateritium* Nees containing the enzyme cyanide hydratase. The spray drier inlet temperature was 150° C. and the outlet temperature was 70° C. The retention of activity of the enzyme in degrading cyanide to formamide over the drier was found to be 100%. In storage it was found that the spray dried cells retained enzyme activity for several months. This compares most favourably with the retention of activity by wet cells of the same microorganism. In the wet cells activity was lost in 7 days.

EXAMPLE 3

The apparatus shown in the FIGURE was used to spray dry cells of the bacterium *Methylophilus methylotrophus* strain AS-1 (NCIB 10515) containing the enzyme amidase. The spray drier inlet temperature was 160° to 180° C. and the outlet temperature was 80° to 90° C. The retention of activity of the enzyme in the decomposition of acrylamide over the drier was found to be 90%. In storage it was found that the spray dried cells retained enzyme activity for several months. This compares most favourably with the retention of activity by wet cells of the same microorganism. In the wet cells activity was lost in 7 days.

EXAMPLE 4

The apparatus shown in the FIGURE was used to spray dry cells of the yeast *Candida utilis* Strain ATCC 8206 containing the enzyme pyruvate decarboxylase. The spray drier inlet temperature was 150° C. and the outlet temperature was 60° C. The retention of activity of the enzyme pyruvate decarboxylase over the drier was found to be 80%. The period of time for which enzyme activity was retained in storage was found to be similar to the period for which activity was retained in wet cells of the same microorganism.

EXAMPLE 5

The apparatus of the FIGURE was used to spray dry cells of the bacterium *Lactobacillus plantarum* strain NCIB 40027. The spray drier inlet temperature was 150° C. and the outlet temperature was 70° C. The retention of activity by the bacterial cells in the glycolitic pathway and in amino acid biosynthesis over the drier was 100%. In storage it was found that the spray dried cells retained activity in the above metabolic pathways for several months. This compares most favourably with the retention of activity by wet cells of the same microorganism. In the wet cells activity was lost in 1 to 2 weeks.

What is claimed is:

1. A method for the production of enzyme-containing biocatalysts which comprises spray drying whole cells of an enzyme-containing microorganism under conditions such that the biocatalytic activity of the enzyme is retained, the microorganism being selected from the group consisting of *Fusarium lateritium* containing the enzyme cyanide hydratase, *Methylophilus methylotrophus* containing the enzyme amidase and *Pseudomonas putida* containing the enzyme D-2-haloalkanoic acid halidohydrolase, and said conditions comprising spray drying using a spray drier with an inlet temperature in the range 140° to 180° C. and an outlet temperature in the range 60° to 90° C. for average periods in the range 15 to 45 seconds.

2. A method according to claim 1 wherein the cells are spray dried when in a suspension having a cell dry weight in the range 6% to 12%.

3. A method for the product ion of enzyme-containing biocatalysts which comprises spray drying whole cells of an enzyme-containing microorganism under conditions such that the biocatalytic activity of the enzyme is retained, the microorganism being selected from the group consisting of strain NCIB 12018, strain NCIB 12158, strain CMI 300533 and strain NCIB 10515, and said conditions comprising spray drying using a spray drier with an inlet temperature in the range 140° to 180° C. and an outlet temperature in the range 60° to 90° C. for average periods in the range 15 to 45 seconds.

4. A method according to claim 3 wherein the cells are spray dried when in a suspension having a cell dry weight in the range 6% to 12%.

5. A method for the production of enzyme-containing biocatalysts which comprises spray drying an aqueous feed of whole cells of an enzyme-containing bacteria wherein the enzyme is selected from the group consisting of amidase and D-2-haloalkanoic acid halide hydrolase, using a spray drier at a temperature such that the spray dried material is discharged at an outlet temperature in the range 60° to 110° C. and the spray drying is accomplished in a time period of up to 45 seconds such that the biocatalyst activity of the enzyme is retained.

* * * * *